United States Patent
Jungwirth et al.

(10) Patent No.: US 9,970,971 B2
(45) Date of Patent: May 15, 2018

(54) FLASHLAMP DEGRADATION MONITORING SYSTEM AND METHOD

(71) Applicant: The Boeing Company, Chicago, IL (US)

(72) Inventors: Douglas R. Jungwirth, Porter Ranch, CA (US); Anton M. Bouckaert, Simi Valley, CA (US)

(73) Assignee: The Boeing Company, Chicago, IL (US)

( * ) Notice: Subject to any disclaimer, the term of this patent is extended or adjusted under 35 U.S.C. 154(b) by 769 days.

(21) Appl. No.: 14/494,145

(22) Filed: Sep. 23, 2014

(65) Prior Publication Data

US 2016/0084896 A1    Mar. 24, 2016

(51) Int. Cl.
| | | |
|---|---|---|
| *G01R 13/00* | (2006.01) | |
| *G01R 29/027* | (2006.01) | |
| *G01R 17/00* | (2006.01) | |
| *G01R 19/00* | (2006.01) | |
| *G01N 21/88* | (2006.01) | |
| *G01J 1/42* | (2006.01) | |

(52) U.S. Cl.
CPC .............. *G01R 29/027* (2013.01); *G01J 1/42* (2013.01); *G01N 21/88* (2013.01); *G01R 17/00* (2013.01); *G01R 19/0046* (2013.01); *G01J 2001/4238* (2013.01); *G01N 2201/088* (2013.01)

(58) Field of Classification Search
CPC .. G01R 29/027; G01R 17/00; G01R 19/0046; G01J 1/42; G01J 2001/4238; G01N 21/88; G01N 2201/088
USPC .......................................................... 702/66
See application file for complete search history.

(56) References Cited

U.S. PATENT DOCUMENTS

| | | | | |
|---|---|---|---|---|
| 3,996,494 A | * | 12/1976 | Suga .................. | H05B 41/3922 250/205 |
| 4,707,796 A | * | 11/1987 | Calabro .................. | G07C 3/00 702/34 |
| 4,810,936 A | * | 3/1989 | Nuckolls ................ | H05B 37/03 315/119 |
| 4,831,564 A | * | 5/1989 | Suga ........................ | G07C 3/00 324/414 |
| 4,952,972 A | * | 8/1990 | Someya ............. | H04N 1/00002 250/226 |
| 5,019,751 A | * | 5/1991 | Flory, IV ............... | H05B 37/03 315/119 |
| 5,479,159 A | * | 12/1995 | Kelly .................. | H02J 13/0089 315/119 |
| 5,578,998 A | * | 11/1996 | Kasprowicz ........... | G01R 31/44 315/131 |
| 6,028,396 A | * | 2/2000 | Morrissey, Jr. ........ | H05B 37/03 315/119 |

(Continued)

OTHER PUBLICATIONS

"The ABC's of High Intensity Discharge (HID) Ballasts," Advance Transformer Co. (2005).

*Primary Examiner* — Stephanie Bloss
(74) *Attorney, Agent, or Firm* — Walters & Wasylyna LLC

(57) ABSTRACT

A method for monitoring degradation of a flashlamp including triggering the flashlamp to produce a light pulse, monitoring at least one parameter as a function of time to obtain a pulse waveform of the light pulse, comparing the pulse waveform to at least one reference pulse waveform to determine a difference therebetween, and flagging an end-of-lamp-life condition when the difference exceeds a predetermined threshold.

22 Claims, 15 Drawing Sheets

(56) References Cited

U.S. PATENT DOCUMENTS

| | | | | |
|---|---|---|---|---|
| 6,413,210 B1* | 7/2002 | Enomoto | ............ | A61B 1/00055 |
| | | | | 362/574 |
| 6,452,339 B1* | 9/2002 | Morrissey | .............. | H05B 37/03 |
| | | | | 315/119 |
| 6,734,642 B1* | 5/2004 | Reverberi | ............ | H05B 37/034 |
| | | | | 315/308 |
| 6,784,667 B2* | 8/2004 | Belenger | ................ | G01R 31/44 |
| | | | | 324/414 |
| 7,009,829 B2* | 3/2006 | Lentz | ................ | H05B 41/2856 |
| | | | | 361/103 |
| 7,382,454 B1* | 6/2008 | Turner | ...................... | G01J 1/42 |
| | | | | 250/226 |
| 8,274,649 B2* | 9/2012 | Hamilton, II | ......... | G01J 1/4228 |
| | | | | 315/291 |
| 9,784,679 B2* | 10/2017 | Rothberg | ........... | G01N 21/6408 |
| 2008/0298043 A1* | 12/2008 | Shimotomai | .............. | G01J 1/32 |
| | | | | 362/1 |
| 2011/0187920 A1* | 8/2011 | Shimada | ................ | H04N 5/222 |
| | | | | 348/371 |
| 2013/0127372 A1* | 5/2013 | Mirsky | ................ | H05B 41/382 |
| | | | | 315/307 |
| 2014/0265900 A1* | 9/2014 | Sadwick | ............ | H05B 33/0803 |
| | | | | 315/200 R |
| 2016/0003946 A1* | 1/2016 | Gilliland | ................ | G01S 17/10 |
| | | | | 356/5.01 |

* cited by examiner

FLASHLAMP DEGRADATION MONITORING SYSTEM AND METHOD

FIELD

This application relates to flashlamps and, more particularly, to monitoring techniques for gas discharge flashlamps.

BACKGROUND

High-intensity discharge lamps are relatively compact and lightweight, yet they are capable of producing a significant amount of illumination. Furthermore, the bright white spectral profile of high-intensity discharge lamps, such as xenon arc lamps, closely resembles natural sunlight. Therefore, high-intensity discharge lamps are commonly used in solar simulators, such as for testing solar cells under carefully controlled laboratory conditions.

Continuous operation of high-intensity discharge lamps requires a significant amount of electrical energy and produces a significant amount of unwanted heat. Therefore, gas discharge flashlamps, such as xenon flashlamps, are often used, particularly when a large area (e.g., a large solar panel or solar array) is being illuminated. Gas discharge flashlamps produce a spectral profile that mimics solar illumination, but only for a brief moment (e.g., 1 or 2 milliseconds), thereby consuming significantly less energy and producing significantly less heat than continuously operated lamps.

Gas discharge flashlamps typically require a high-voltage trigger that creates initial gas ionization that, in turn, facilitates a high-current pulse through the flashlamp. The initial high-voltage trigger and subsequent high-current pulse form a high-pressure plasma within the flashlamp, which may degrade the flashlamp and, ultimately, may cause the flashlamp to fail (e.g., break).

Attempts have been made to avoid an in-service failure of a flashlamp. For example, a flashlamp can be visually inspected from time to time to determine whether the flashlamp has reached an end-of-lamp-life condition. However, such visual inspections tend to interfere with normal flashlamp operation. As another example, a flashlamp can be taken out of service after a predetermined number of pulses. However, doing so can be wasteful if the flashlamp still has a useful life.

Accordingly, those skilled in the art continue with research and development efforts in the field of flashlamps.

SUMMARY

In one embodiment, the disclosed method for monitoring degradation of a flashlamp may include the steps of (1) triggering the flashlamp to produce a light pulse; (2) monitoring at least one parameter as a function of time to obtain a pulse waveform of the light pulse; (3) comparing the pulse waveform to at least one reference pulse waveform to determine a difference therebetween; and (4) flagging an end-of-lamp-life condition when the difference exceeds a predetermined threshold.

In another embodiment, the disclosed flashlamp degradation monitoring system may include a flashlamp that includes an envelope housing an ionizable gas and opposed electrodes, a power supply electrically coupled to the electrodes, a trigger positioned to initiate ionization of the ionizable gas and generate a light pulse, a sensor positioned to monitor at least one parameter as a function of time, thereby yielding a pulse waveform for the light pulse, and a computer in communication with the sensor, wherein the computer is configured to compare the pulse waveform with at least one reference pulse waveform.

In another embodiment, the disclosed flashlamp degradation monitoring system may include a flashlamp that includes an envelope housing an ionizable gas and opposed electrodes, a power supply electrically coupled to the electrodes, a trigger positioned to initiate ionization of the ionizable gas and generate a light pulse, an electronic sensor positioned to monitor electric current and/or voltage as a function of time, thereby yielding a pulse waveform for the light pulse, and a computer in communication with the electronic sensor, wherein the computer is configured to compare the pulse waveform with at least one reference pulse waveform.

In yet another embodiment, the disclosed flashlamp degradation monitoring system may include a flashlamp that includes an envelope housing an ionizable gas and opposed electrodes, a power supply electrically coupled to the electrodes, a trigger positioned to initiate ionization of the ionizable gas and generate a light pulse, an optical detector positioned to monitor light energy as a function of time, thereby yielding a pulse waveform for the light pulse, and a computer in communication with the optical detector, wherein the computer is configured to compare the pulse waveform with at least one reference pulse waveform.

Other embodiments of the disclosed flashlamp degradation monitoring system and method will become apparent from the following detailed description, the accompanying drawings and the appended claims.

DETAILED DESCRIPTION

Figure 1:
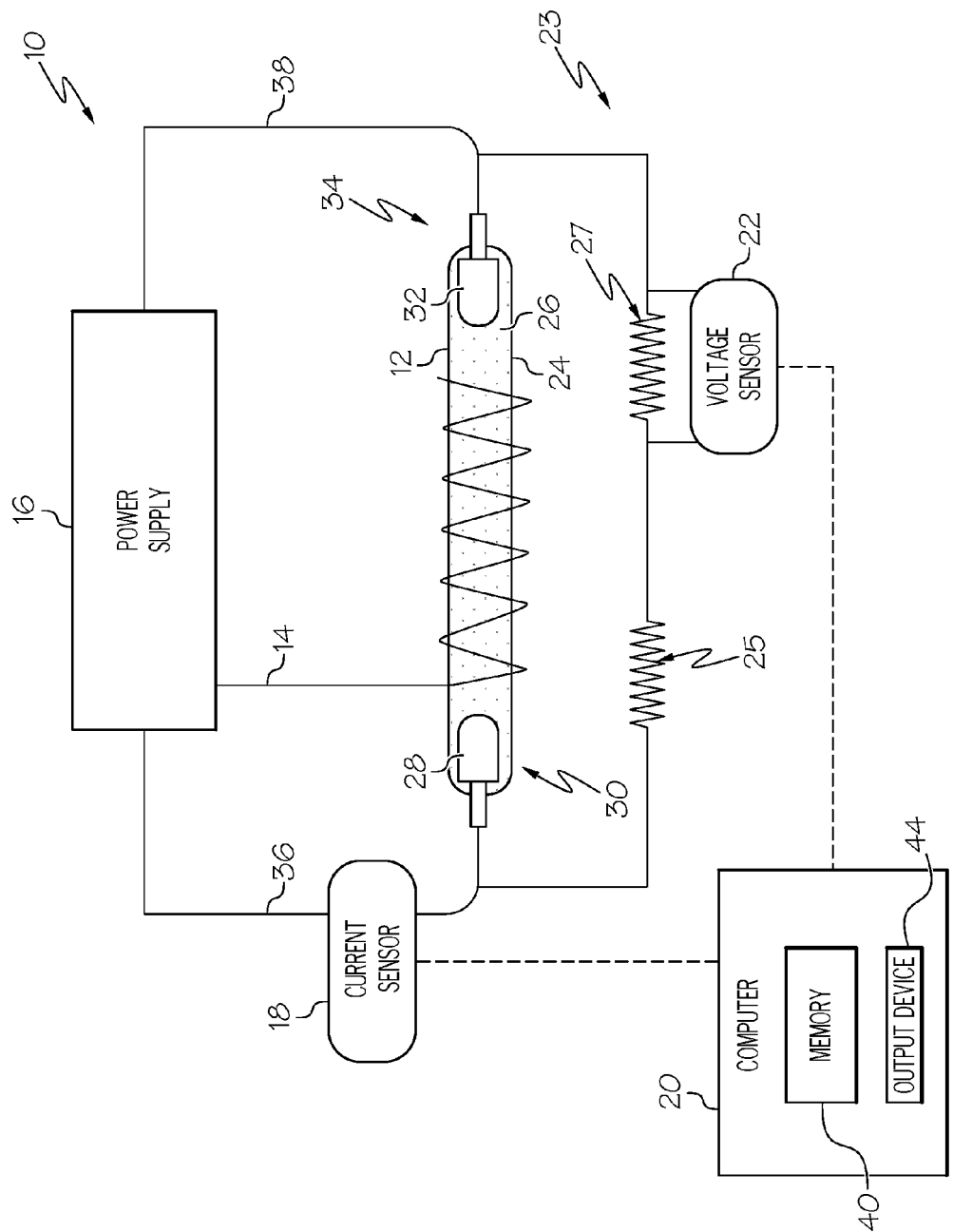
FIG. 1 is a schematic representation of one embodiment of the disclosed flashlamp degradation monitoring system.

Referring to FIG. 1, one embodiment of the disclosed flashlamp degradation monitoring system, generally designated 10, may include a flashlamp 12, a trigger 14, a power supply 16, a current sensor 18 and a computer 20. Additionally, or as an alternative to the current sensor 18, the disclosed flashlamp degradation monitoring system 10 may include a voltage sensor 22.

The flashlamp 12 may be any lamp capable of generating a light pulse (or a series of light pulses) using electrical energy. In one particular construction, the flashlamp 12 may be a gas discharge flashlamp, such as a xenon flashlamp or a krypton flashlamp. As one specific, non-limiting example, the flashlamp 12 may be a Pulsed Xenon lamp commercially available from Excelitas Technologies Corp. of Waltham, Mass.

The flashlamp 12 may include a sealed envelope 24, such as a glass tube, which may have various shapes (e.g., straight, U-shaped, circular, etc.). The sealed envelope 24 may contain a quantity of ionizable gas 26, such as a noble gas (e.g., xenon and/or argon). A first electrode 28 may be sealed in the envelope 24 proximate (at or near) a first end 30 of the envelope 24. The first electrode 28 may be electrically coupled with the power supply 16. A second electrode 32 may be sealed in the envelope 24 proximate a second end 34 of the envelope 24. The second electrode 32 may be opposed from the first electrode 28, and may be electrically coupled with the power supply 16.

The trigger 14 may be positioned proximate the flashlamp 12 to supply a high-voltage (e.g., 25,000 volts) trigger pulse that initiates ionization of the ionizable gas 26, thereby reducing the effective resistance across the first and second electrodes 28, 32 and allowing electric current to flow between the first and second electrodes 28, 32. The trigger 14 may be electrically coupled to the power supply 16 by way of appropriate circuitry configured to yield the required high voltage (low current).

As shown in FIG. 1, the trigger 14 may include a coil wrapped around the envelope 24 of the flashlamp 12. However, various triggers (e.g., plate triggers) may be capable of supplying the required high-voltage trigger pulse and may be used without departing from the scope of the present disclosure.

The power supply 16 may be configured to pass a high-current pulse between the first and second electrodes 28, 32 when the trigger 14 initiates ionization of the ionizable gas 26 within the flashlamp 12. For example, the power supply 16 may include a direct current source that charges one or more capacitors (e.g., plural capacitors electrically arranged in parallel). The capacitors may rapidly discharge upon initial ionization of the ionizable gas 26 by the trigger 14, thereby creating a high-pressure plasma and a corresponding light pulse. The light pulse may have a duration ranging from about 0.001 seconds (1 millisecond) to about 0.005 seconds, such as from about 0.001 seconds to about 0.003 seconds.

The current sensor 18 may be positioned to monitor the electric current flowing through the flashlamp 12 during each light pulse. For example, the current sensor 18 may be coupled to the supply line 36 that electrically couples the first electrode 28 with the power supply 16, as shown in FIG. 1, or to the supply line 38 that electrically couples the second electrode 32 with the power supply 16. Therefore, electric current may be an electronic parameter monitored by an electronic sensor (the current sensor 18).

The current sensor 18 may be any device that produces a signal indicative of the electric current flowing through the flashlamp 12 at any given time. As one specific, non-limiting example, the current sensor 18 may be (or may include) a Hall effect sensor. As another specific, non-limiting example, the current sensor 18 may be (or may include) a fiber optic current sensor.

The current sensor 18 may be in communication (e.g., one-way or two-way) with the computer 20. The computer 20 may be any processing device that includes, or that is in communication with, memory 40 (e.g., a hard drive, a flash drive, cloud-based data storage, or the like). The current sensor 18 may communicate to the computer 20 the signal indicative of the electric current flowing through the flashlamp 12 as a function of time. The computer 20 may store in memory 40 the electric current versus time data received from the current sensor 18.

The voltage sensor 22 may be positioned to monitor the voltage across the flashlamp 12 during each light pulse. For example, the voltage sensor 22 may be part of a voltage sensing circuit 23 that includes the voltage sensor 22, resistors 25, 27 and the like. The voltage sensing circuit 23 may be electrically coupled to the supply lines 36, 38 to monitor the voltage across the flashlamp 12. Therefore, voltage may be an electronic parameter monitored by an electronic sensor (the voltage sensor 22).

The voltage sensor 22 may be any device or system that produces a signal indicative of (e.g., proportional to) the voltage across the flashlamp 12 at any given time. As one general, non-limiting example, the voltage sensor 22 may be (or may include) a digital voltmeter.

The voltage sensor 22 may be in communication (e.g., one-way or two-way) with the computer 20. The voltage sensor 22 may communicate to the computer 20 the signal indicative of the voltage across the flashlamp 12 as a function of time. The computer 20 may store in memory 40 the voltage versus time data received from the voltage sensor 22.

Each light pulse produced by the flashlamp 12 may have a pulse waveform based on the collected parameter versus time data. In one expression, the pulse waveform may be based on the electric current versus time data received from the current sensor 18. In another expression, the pulse waveform may be based on the voltage versus time data received from the voltage sensor 22.

Figure 2A:
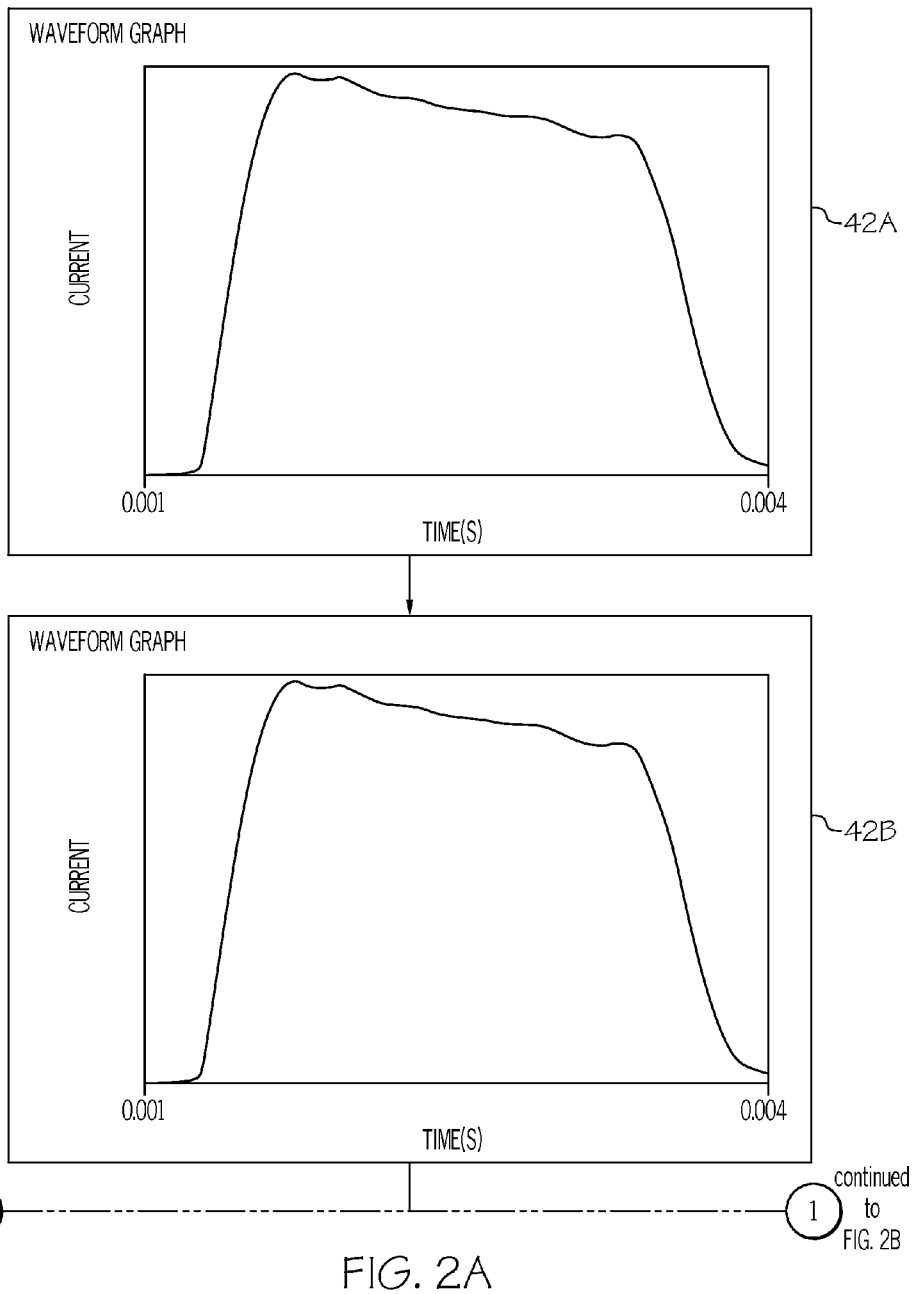
FIGS. 2A-2f are graphical representations of the pulse waveform data collected by the flashlamp degradation monitoring system of FIG. 1.
Figure 2B:
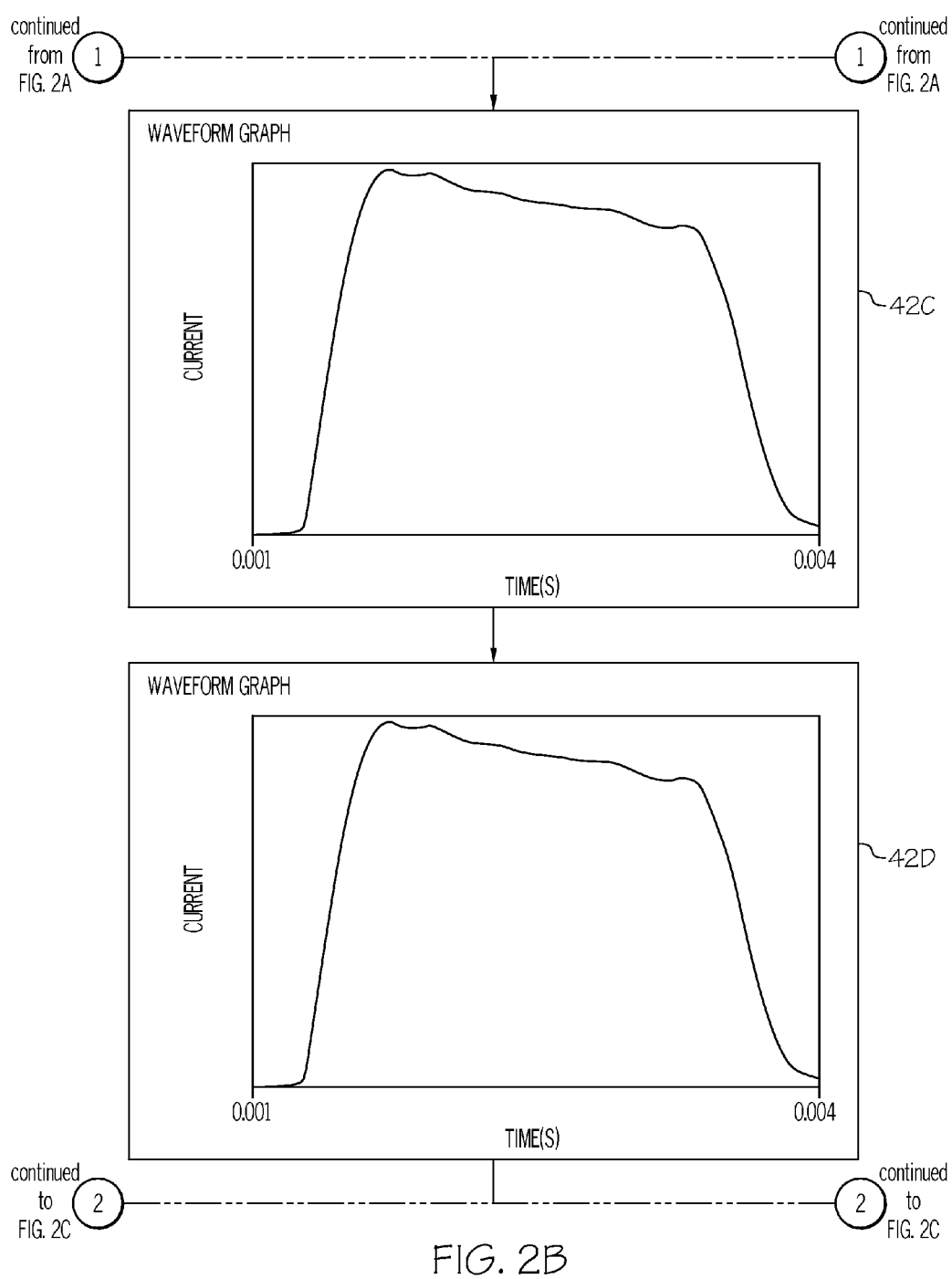
Figure 2C:
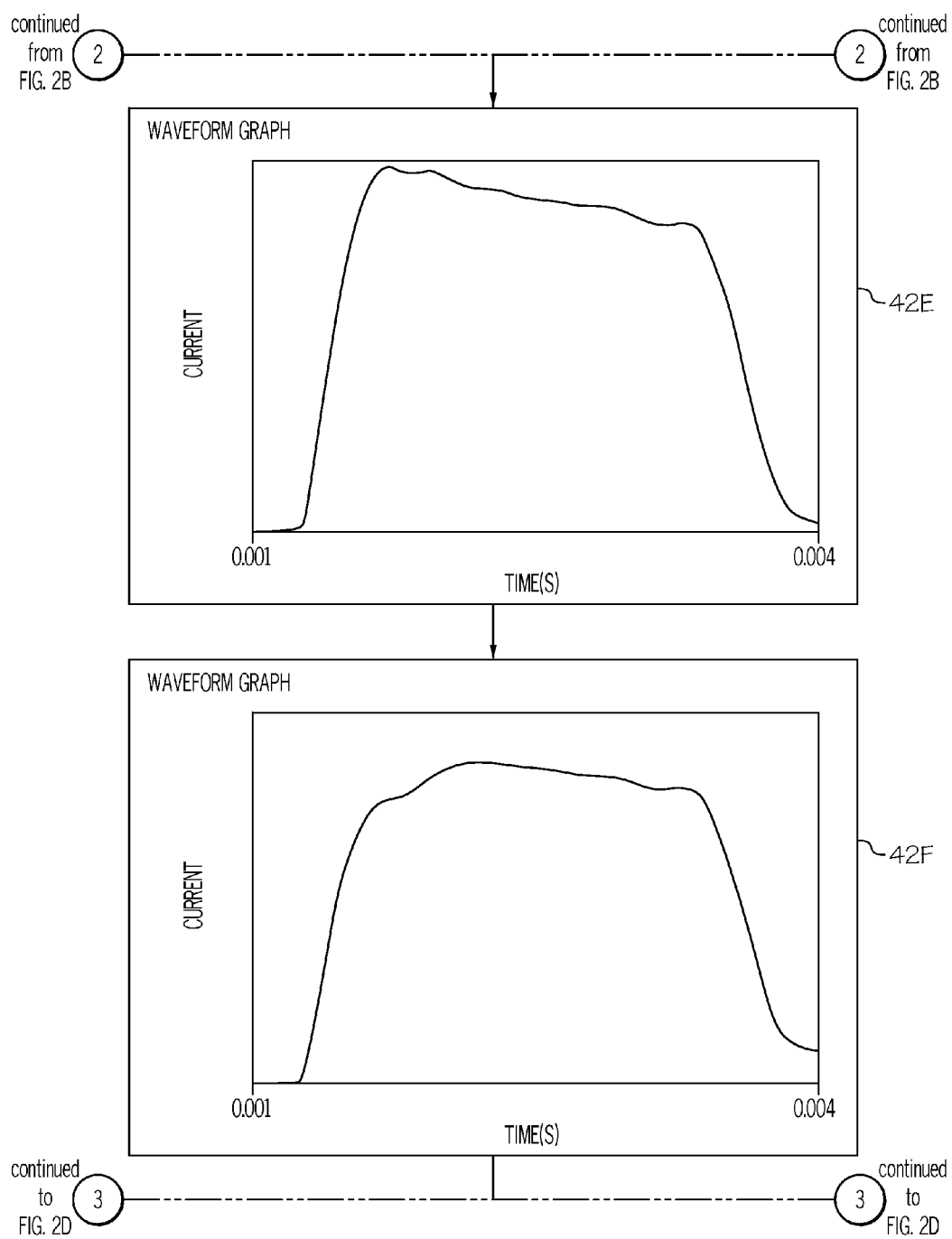
Figure 2D:
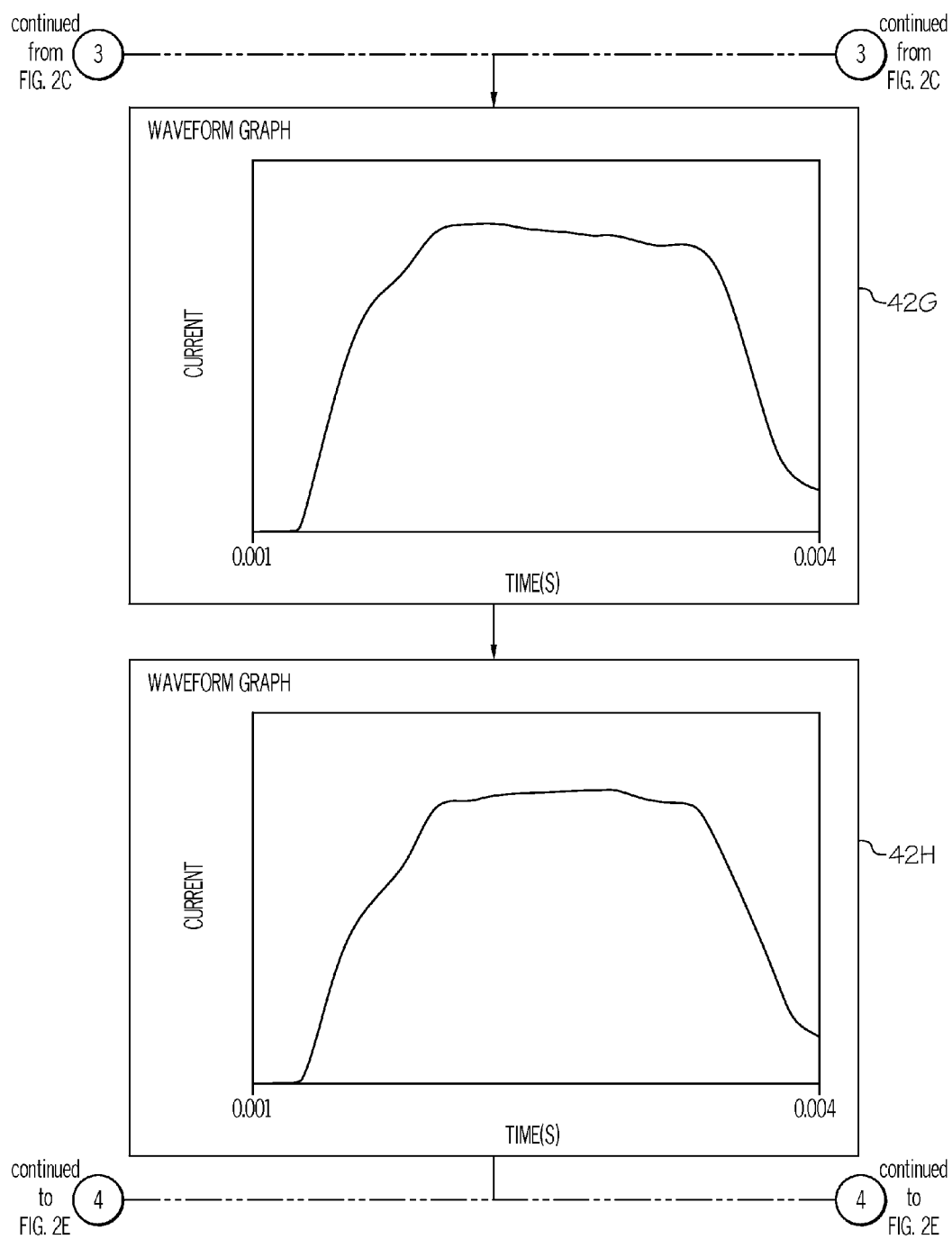
Figure 2E:
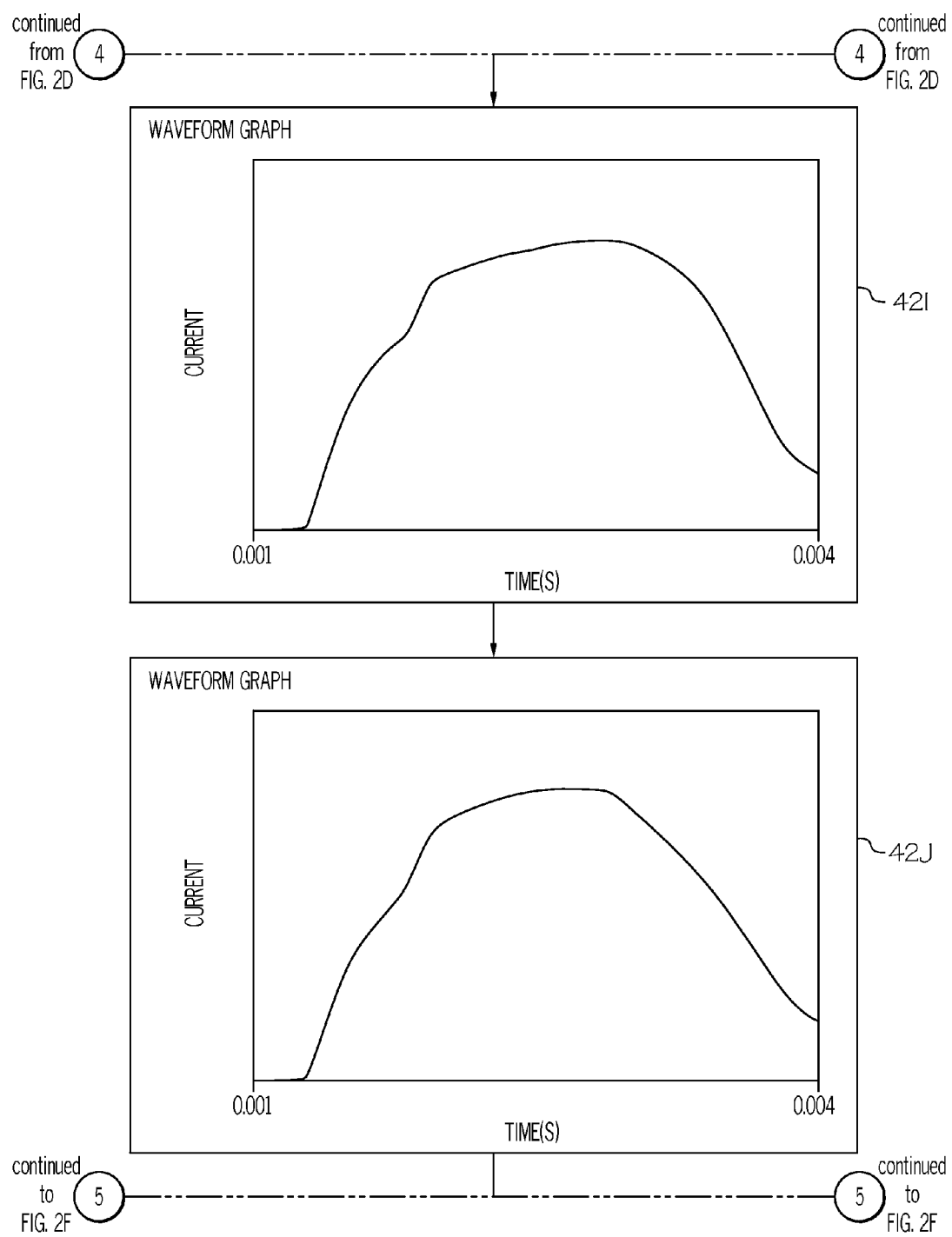
Figure 2F:
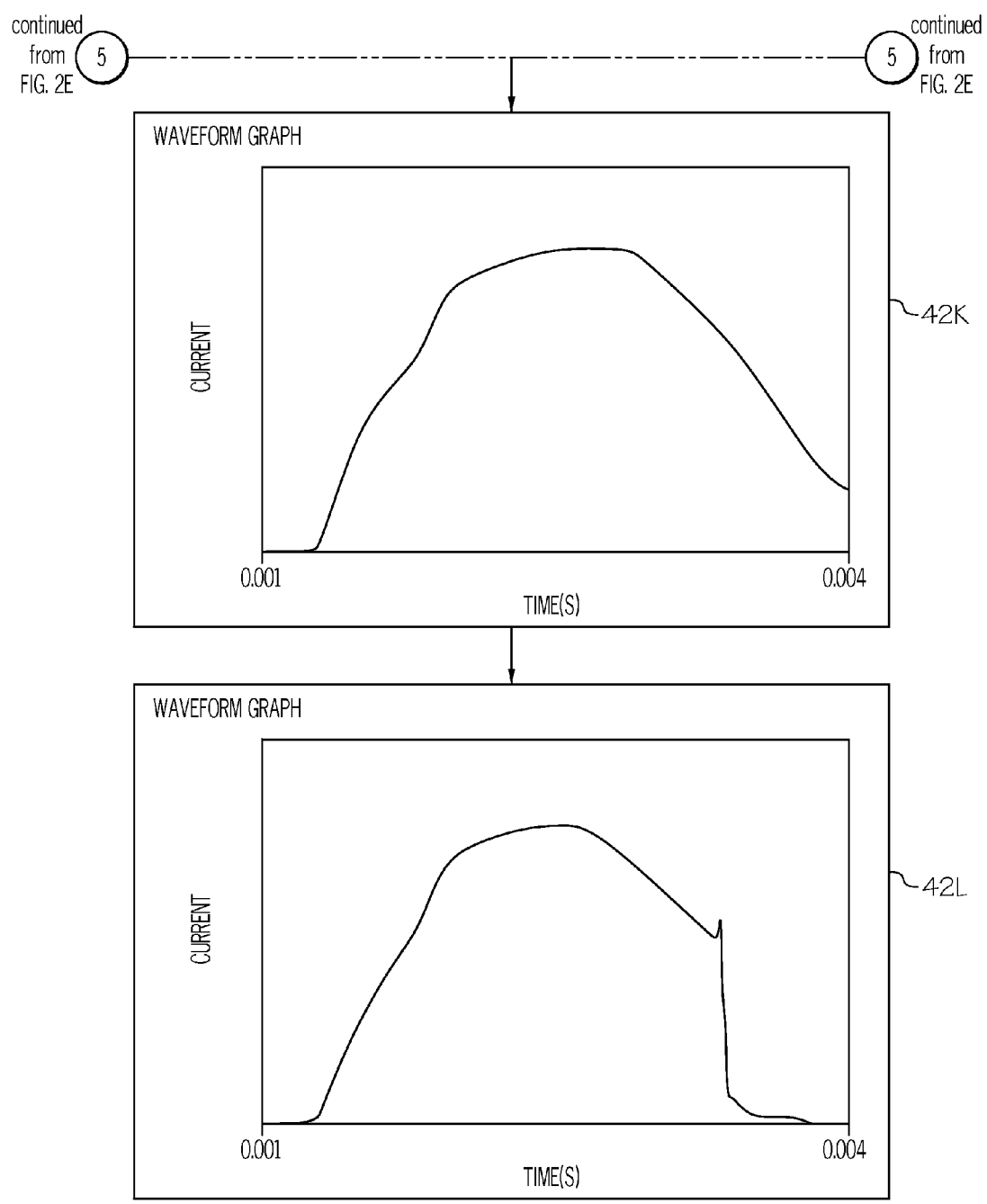

FIGS. 2A-2F depict a series of pulse waveforms 42A, 42B, 42C, 42D, 42E, 42F, 42G, 42H, 42I, 42J, 42K, 42L based on collected electric current versus time data. As shown by pulse waveforms 42A (FIG. 2A), 42B (FIG. 2A), 42C (FIG. 2B), 42D (FIG. 2B), 42E (FIG. 2C), a normal functioning flashlamp 12 may generate light pulses having pulse waveforms that are quite similar in shape. For example, the pulse waveforms 42A, 42B, 42C, 42D, 42E of a normal functioning flashlamp 12 may be substantially square-wave shaped. However, as the flashlamp 12 begins to fail (e.g., an end-of-lamp-life condition approaches or exists), a significant and recognizable change may occur in the pulse waveform, as shown by pulse waveform 42F (FIG. 2C). As failure mode progresses, the changes in the pulse waveforms 42G (FIG. 2D), 42H (FIG. 2D), 42I (FIG. 2E), 42J (FIG. 2E), 42K (FIG. 2F) may become even more pronounced until, ultimately, the flashlamp 12 may fail, as shown by pulse waveform 42L (FIG. 2F).

Thus, an end-of-lamp-life condition may be identified by comparing the pulse waveform of each light pulse with at least one reference pulse waveform. The comparison may be performed by the computer 20 (FIG. 1). The comparison may determine whether a difference between the present pulse waveform and the reference pulse waveform exceeds a predetermined threshold.

In one particular implementation, the reference pulse waveform may be the pulse waveform of a previous light pulse from the same flashlamp 12 (FIG. 1), and may be retrieved from memory 40 (FIG. 1) for comparison purposes. As one example, the pulse waveform of the present light pulse may be compared to the pulse waveforms of all previous light pulses for the same flashlamp 12. As another example, the pulse waveform of the present light pulse may be compared to the pulse waveforms of a select portion (e.g., every five; the last ten; etc.) of previous light pulses for the same flashlamp 12. As yet another example, the pulse waveform of the present light pulse may be compared to the pulse waveform of the immediately previous light pulse.

Various signal processing techniques are well known in the art and may be used to compare a pulse waveform to one or more reference pulse waveforms. Therefore, selection of a particular signal processing technique to make the comparison will not result in a departure from the scope of the present disclosure. While a direct comparison may be made, the pulse waveforms may be normalized. Normalization may be particularly advantageous when the flashlamp 12 (FIG. 1) is cycled through different voltages and currents.

As one specific, non-limiting example, a pulse waveform may be compared with a reference pulse waveform using a cross-correlation analysis (e.g., normalized cross-correlation). For example, a difference D between a reference pulse waveform A(t) and a present pulse waveform B(t) may be calculated using Equation 1:

$$D = \frac{\frac{1}{a_0} \times \frac{1}{b_0} \sum A(t) \times B(t)}{\frac{1}{a_0} \times \frac{1}{a_0} \sum A(t) \times A(t)} \quad \text{(Eq. 1)}$$

where $a_0$ is the area under the reference pulse waveform A(t) and $b_0$ is the area under the present pulse waveform B(t). An end-of-lamp-life condition may be flagged when the difference D exceeds a predetermined threshold.

As another specific, non-limiting example, a pulse waveform may be compared with a reference pulse waveform using a derivative analysis. The derivative of the pulse waveform may indicate the slope of the waveform over a time interval (e.g., the entire light pulse duration or a portion of the light pulse). An end-of-lamp-life condition may be flagged when the derivative exceeds a predetermined threshold.

As yet another specific, non-limiting example, a pulse waveform may be compared with a reference pulse waveform using a linear approximation analysis over a time interval (e.g., the entire light pulse duration or a portion of the light pulse). A standard deviation may be calculated. An end-of-lamp-life condition may be flagged when the standard deviation exceeds a predetermined threshold.

A user may set the predetermined threshold at which an end-of-lamp-life condition is flagged. The predetermined threshold may be set to accommodate a certain amount of variability from pulse waveform to pulse waveform without flagging an end-of-lamp-life condition. For example, the predetermined threshold may be set at a magnitude sufficient to allow normal pulse waveform-to-pulse waveform variation without flagging the end-of-lamp-life condition. An acceptable level of variability may be dictated by various factors, including inherent variability of the power supply 16 (FIG. 1). For example, variability from pulse waveform to pulse waveform within 10 percent or less (e.g., 5 percent or less) may be acceptable for a normal functioning flashlamp 12 (FIG. 1). Therefore, the predetermined threshold may be set outside what a user may consider normal, acceptable variability. For example, the predetermined threshold may be set at a variability of about 15 percent, such as a variability of about 20 percent or a variability of about 30 percent or a variability of about 40 percent or a variability of about 50 percent.

As used herein, flagging an end-of-lamp-life condition may include identifying the presence of an end-of-lamp-life condition, as well as providing an indication that the end-of-lamp-life condition is present and/or undertaking an action in response to the end-of-lamp-life condition. Referring again to FIG. 1, the computer 20 may include an output device 44, which may include any device that outputs information to the user. For example, the output device 44 may include, but is not limited to, a display (e.g., a screen, a light, a beacon of the like) and/or a speaker. Therefore, flagging an end-of-lamp-life condition may include actuating the output device 44 of the computer 20 to provide a visual and/or audible indication to a user.

In one specific realization, flagging an end-of-lamp-life condition may include disabling the power supply 16 or otherwise preventing further firing of the flashlamp 12. For example, when the computer 20 determines that an end-of-lamp-life condition is present, the computer 20 may communicate a command signal to the power supply 16 to prevent further firing of the flashlamp 12.

Figure 3:
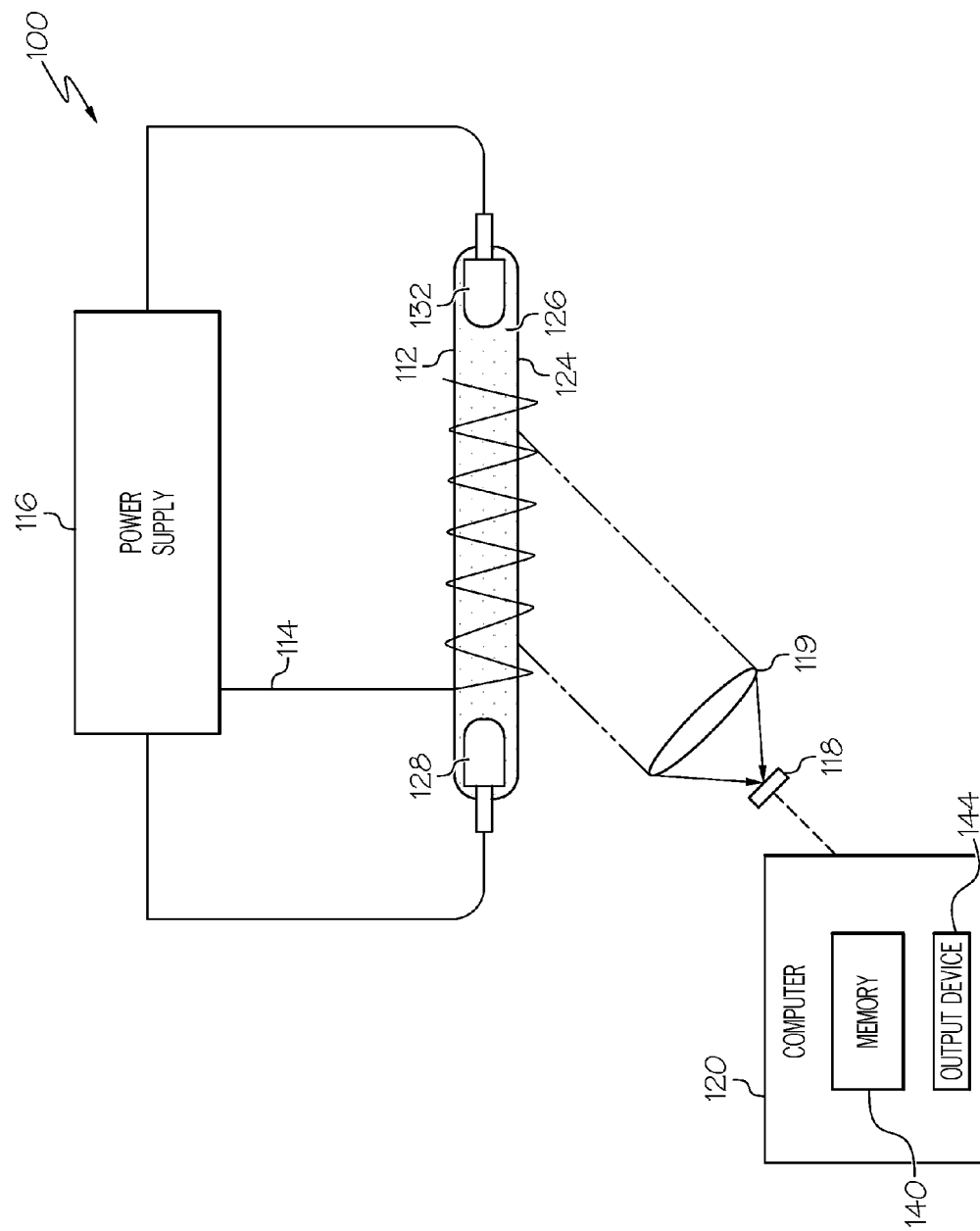
FIG. 3 is a schematic representation of another embodiment of the disclosed flashlamp degradation monitoring system.

Referring to FIG. 3, another embodiment of the disclosed flashlamp degradation monitoring system, generally designated 100, may include a flashlamp 112, a trigger 114, a power supply 116, an optical detector 118 and a computer 120. The flashlamp 112 may include an envelope 124 containing an ionizable gas 126 and electrodes 128, 132. The computer 120 may include memory 140 and an output device 144.

The configuration of flashlamp degradation monitoring system 100 may be substantially the same or similar to the configuration of flashlamp degradation monitoring system 10, with the exception that flashlamp degradation monitoring system 100 may optically monitor the light pulses produced by the flashlamp 112, while flashlamp degradation monitoring system 10 may electronically monitor the light pulses produced by the flashlamp 12. Specifically, rather than electronically monitoring parameters such as electric current and/or voltage, flashlamp degradation monitoring system 100 may utilize the optical detector 118 to monitor the magnitude of the light generated by each light pulse of the flashlamp 112.

The optical detector 118 may be positioned to observe the light pulses generated by the flashlamp 112. For example, a lens 119 may be positioned between the optical detector 118 and the flashlamp 112 to focus the light generated by the flashlamp 112 (at least a portion thereof) onto the optical detector 118. Therefore, light energy/power (number of impinging photons) may be an optical parameter monitored by the optical detector 118.

The optical detector 118 may be any device or system that produces a signal indicative of the energy of the light pulse at any given time. As one general, non-limiting example, the optical detector 118 may be (or may include) a photodetector. As one specific, non-limiting example, the optical detector 118 may be (or may include) a photovoltaic (e.g., solar) cell.

The optical detector 118 may be in communication (e.g., one-way or two-way) with the computer 120. The optical detector 118 may communicate to the computer 120 the signal indicative of the energy of the light pulse as a function of time. The computer 120 may store in memory 140 the light energy versus time data received from the optical detector 118.

Figure 4A:
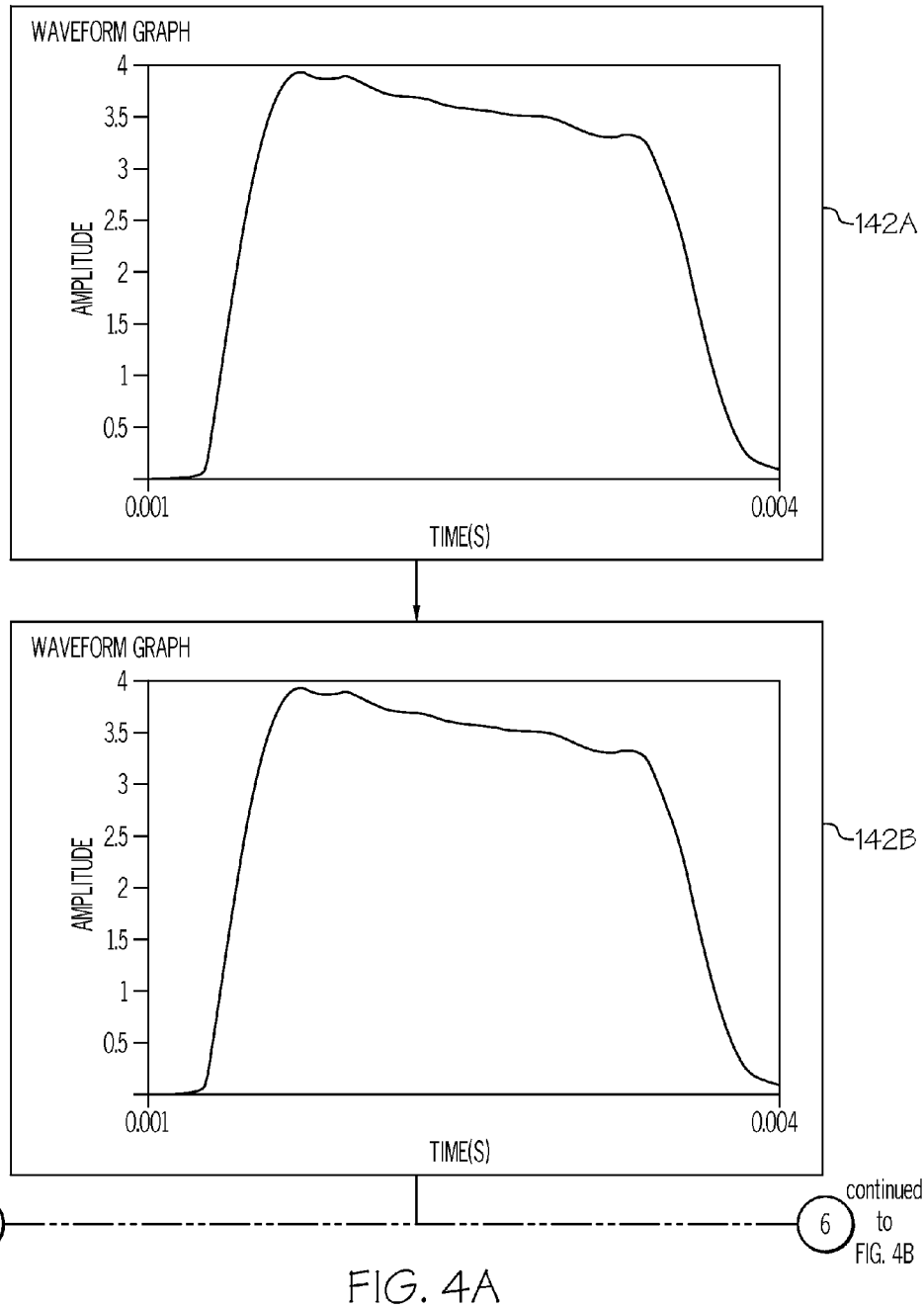
FIGS. 4A-4F are graphical representations of the pulse waveform data collected by the flashlamp degradation monitoring system of FIG. 3.
Figure 4B:
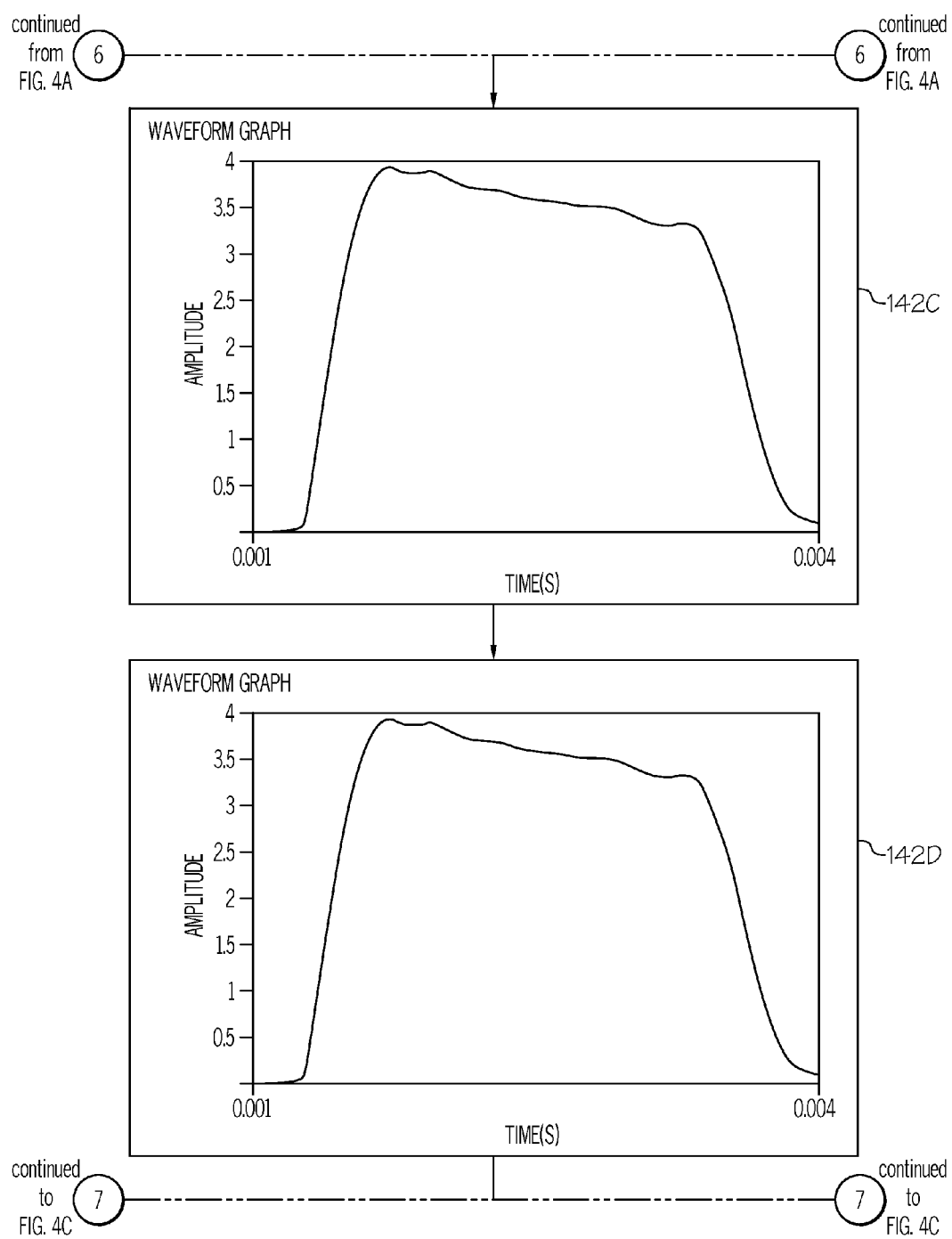
Figure 4C:
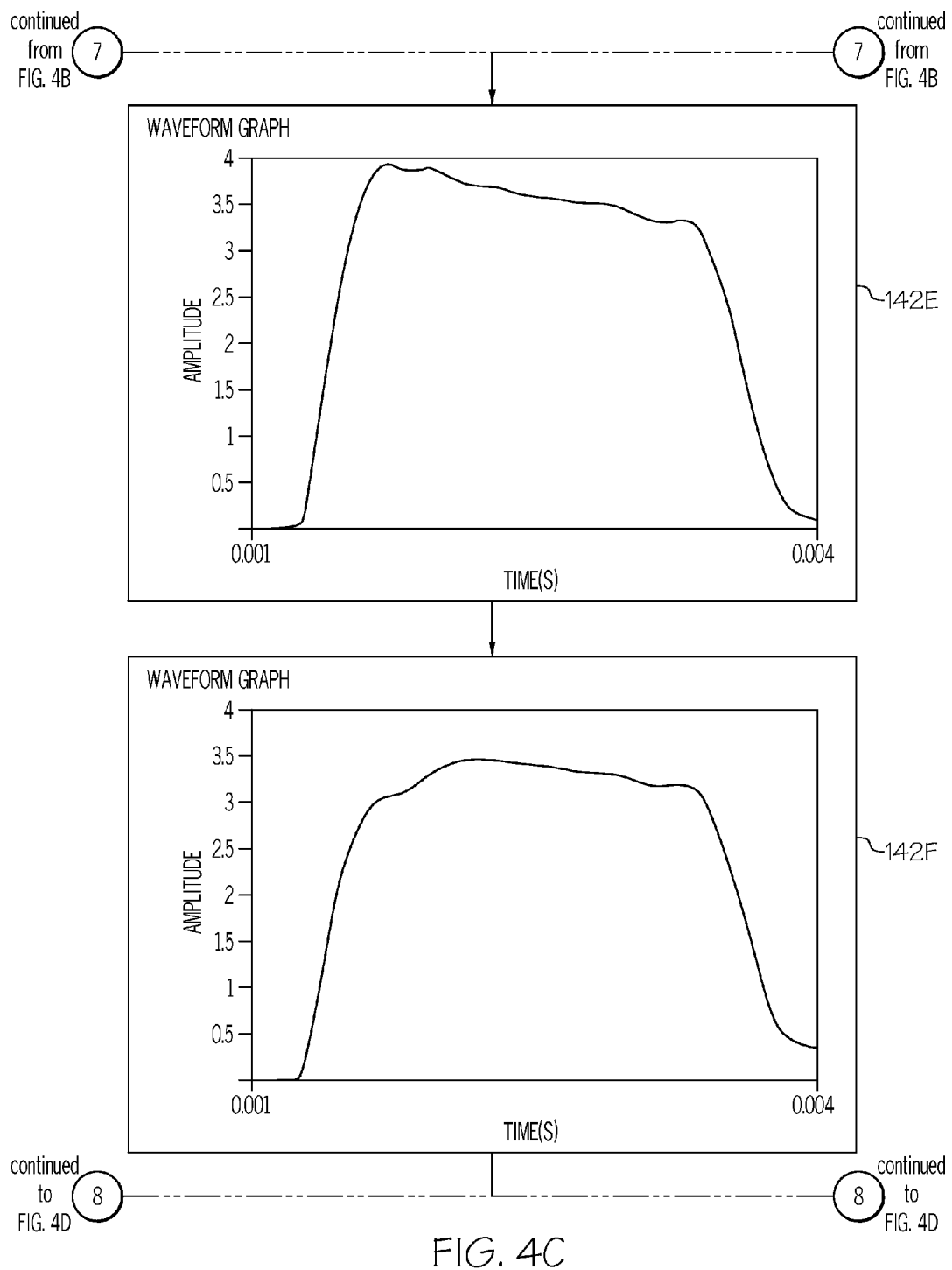
Figure 4D:
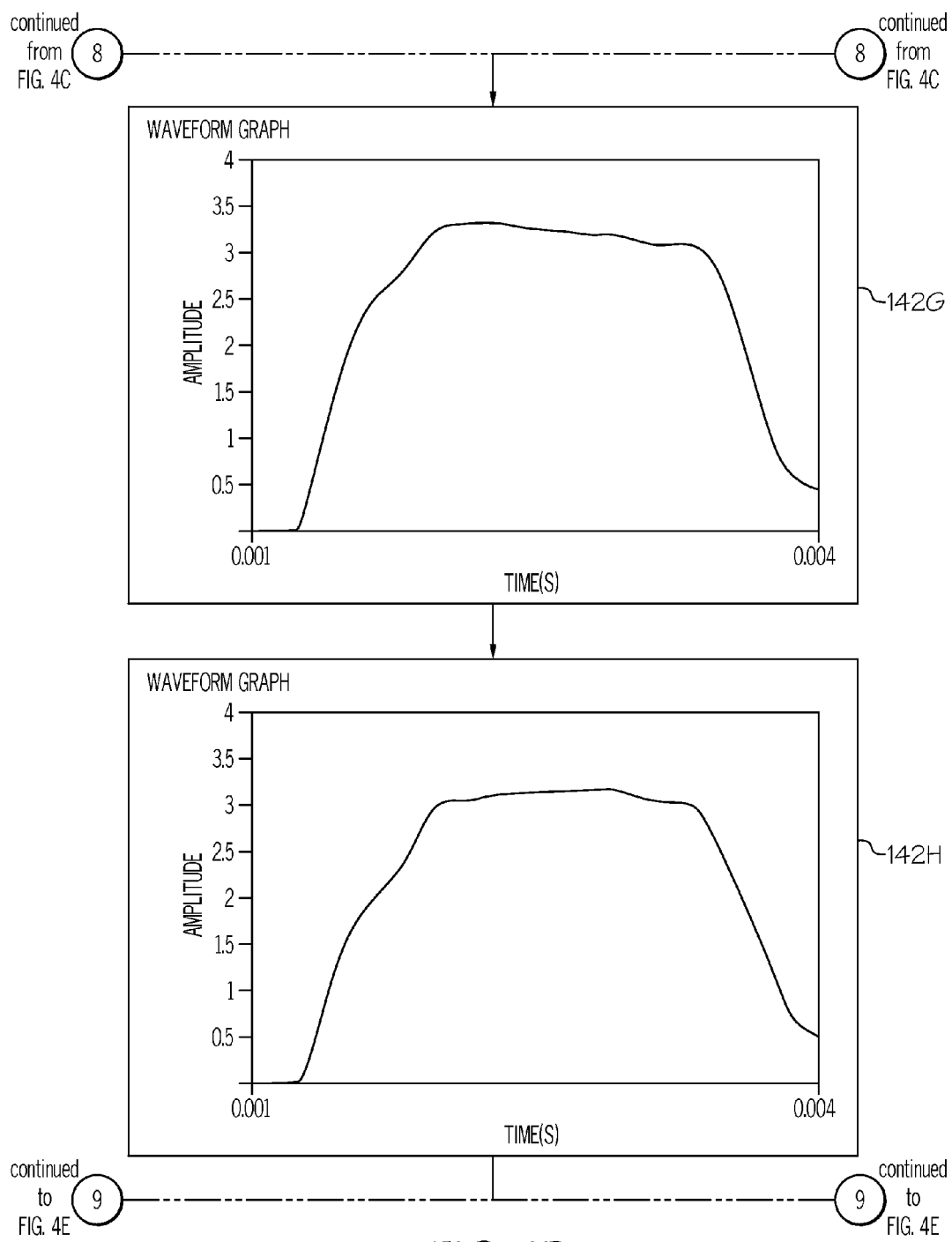
Figure 4E:
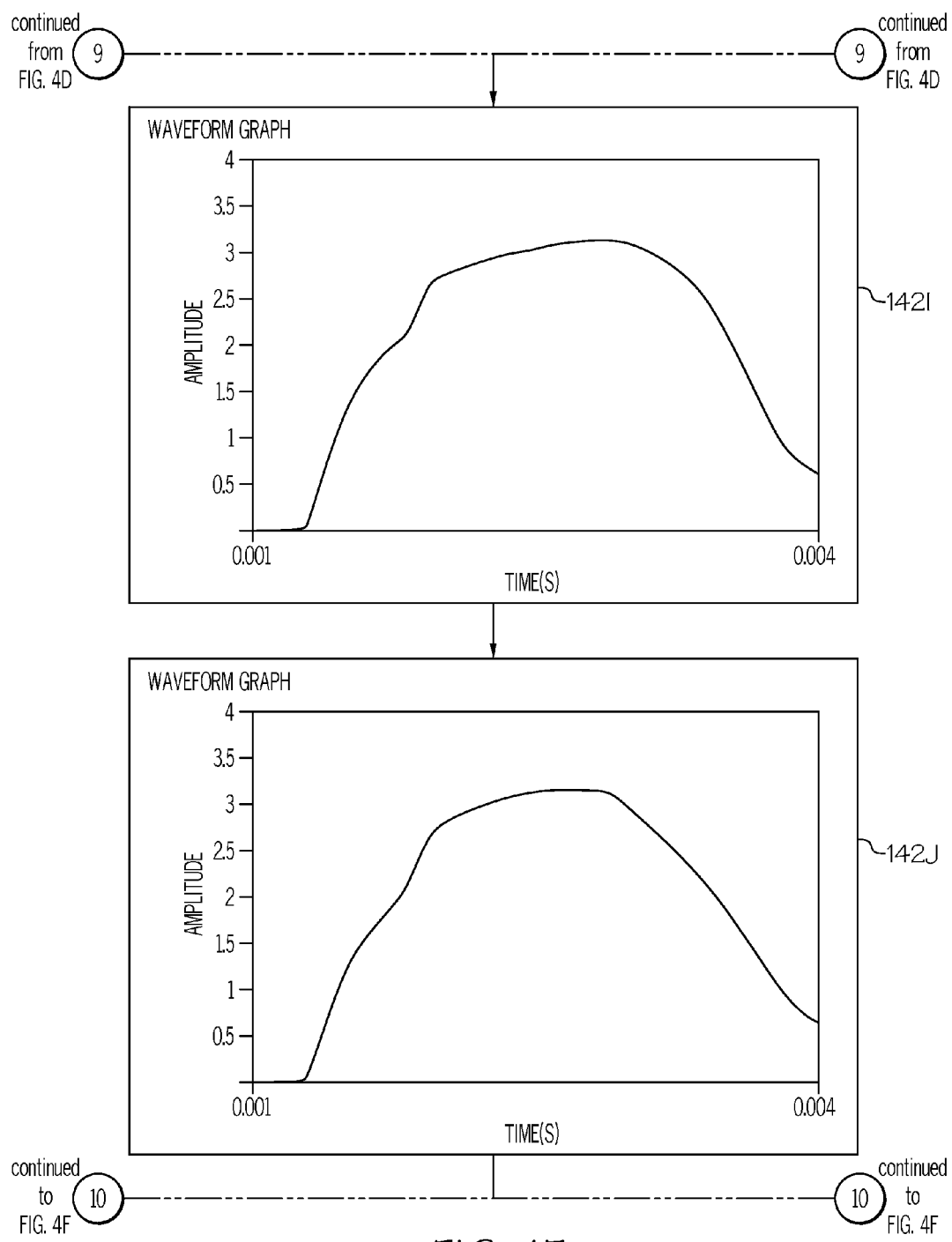
Figure 4F:
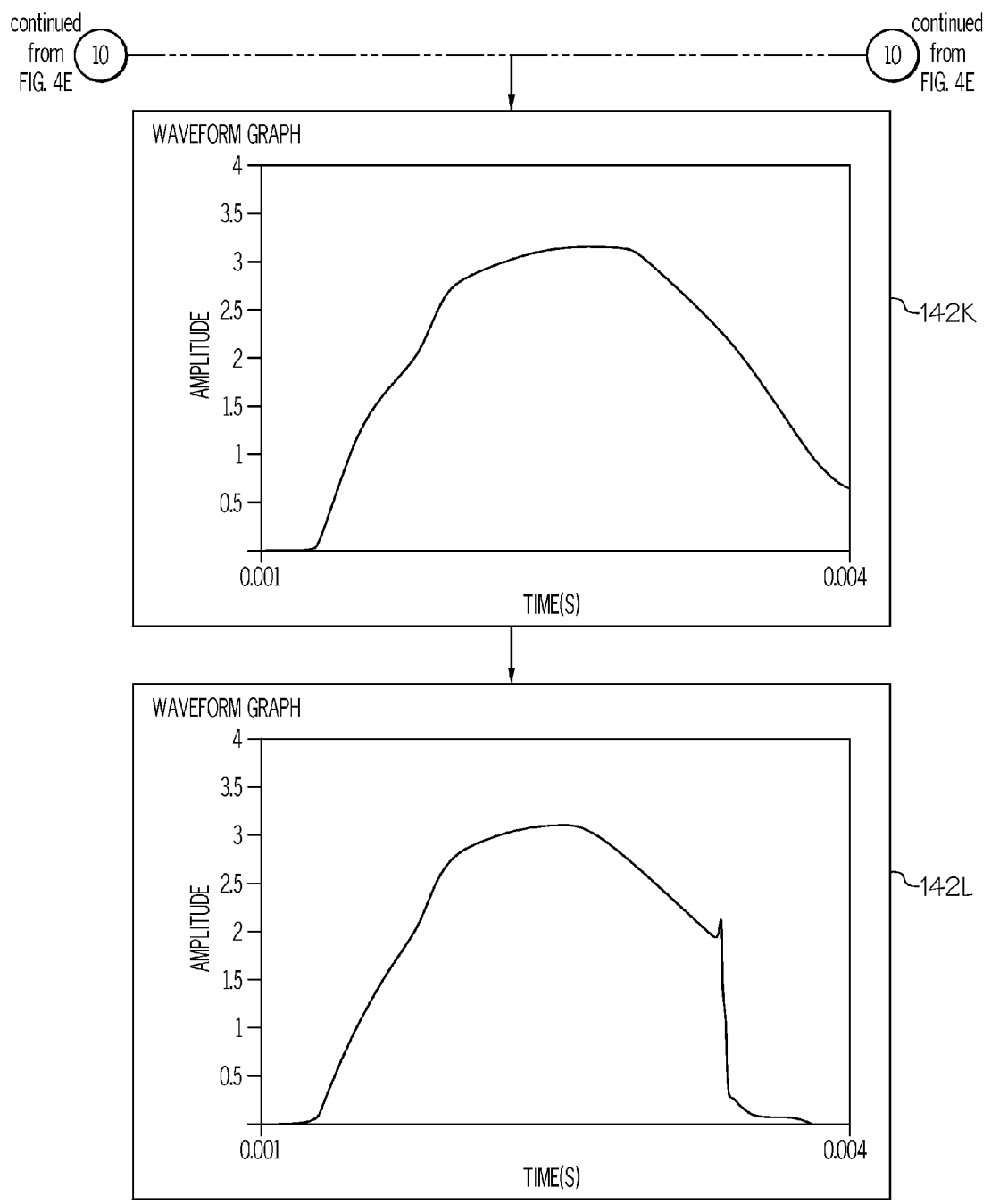

FIG. 4A-4F depict a series of pulse waveforms 142A, 142B, 142C, 142D, 142E, 142F, 142G, 142H, 142I, 142J, 142K, 142L based on collected light energy versus time data. As shown by pulse waveforms 142A (FIG. 4A), 142B (FIG. 4A), 142C (FIG. 4B), 142D (FIG. 4B), 142E (FIG. 4C), a normal functioning flashlamp 112 may generate light pulses having pulse waveforms that are quite similar in shape. For example, the pulse waveforms 142A, 142B, 142C, 142D, 142E of a normal functioning flashlamp 112 may be substantially square-wave shaped. However, as the flashlamp 112 begins to fail (e.g., an end-of-lamp-life condition approaches or exists), a significant and recognizable change may occur in the pulse waveform, as shown by pulse waveform 142F (FIG. 4C). As failure mode progresses, the changes in the pulse waveforms 142G (FIG. 4D), 142H (FIG. 4D), 142I (FIG. 4E), 142J (FIG. 4E), 142K (FIG. 4F) may become even more pronounced until, ultimately, the flashlamp 112 may fail, as shown by pulse waveform 142L (FIG. 4F).

Thus, an end-of-lamp-life condition may be identified by comparing the pulse waveform of each light pulse with at least one reference pulse waveform. The comparison may be performed by the computer 120 (FIG. 3). The comparison may determine whether a difference between the present pulse waveform and the reference pulse waveform exceeds a predetermined threshold. An end-of-lamp-life condition may be flagged when the difference exceeds the predetermined threshold value.

Figure 5:
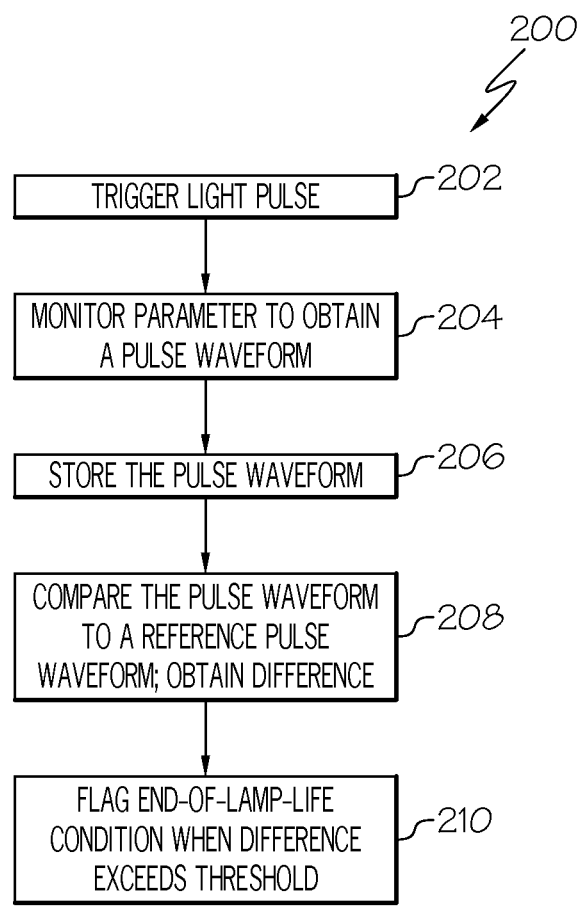
FIG. 5 is a flow diagram depicting one embodiment of the disclosed flashlamp degradation monitoring method.

Referring FIG. 5, the disclosed flashlamp degradation monitoring method, generally designated 200, may be used to determine whether a particular flashlamp has reached an end-of-lamp-life condition. When an end-of-lamp-life condition is flagged, appropriate action may be taken. For example, a warning may be issued and/or the flashlamp may be disabled or taken out of service.

At Block 202, the method 200 may begin by triggering the flashlamp to produce a light pulse. The triggering step (Block 202) may include applying to the flashlamp a voltage pulse of sufficiently high magnitude (but low current) to that initiates ionization of the ionizable gas sealed within the flashlamp. Once ionization is initiated, a high-current pulse may pass through the flashlamp, thereby generating the light pulse.

At Block 204, at least one parameter may be monitored during the light pulse to obtain a pulse waveform for the light pulse. In one variation, an electronic parameter, such as electric current and/or voltage, may be monitored using an electronic sensor (e.g., a current sensor and/or a voltage sensor) to obtain the pulse waveform. In another variation, an optical parameter, such as light energy (e.g., number of photons), may be monitored using an optical detector to obtain the pulse waveform.

At Block 206, the pulse waveform may be stored. For example, the pulse waveform may be stored by a computer in suitable memory such that the stored pulse waveform data may be retrieved in the future and, for example, used as a reference pulse waveform.

At Block 208, the pulse waveform may be compared to at least one reference pulse waveform. The reference pulse waveform may be the pulse waveform of a previous light pulse, such as a previous light pulse from the same flashlamp. The comparison may ascertain a difference between the pulse waveform and the at least one reference pulse waveform. Various signal processing techniques may be used to ascertain the difference between the pulse waveform and the reference pulse waveform.

At Block 210, an end-of-lamp-life condition may be flagged when the difference obtained in Block 208 (e.g., the difference between the present pulse waveform and a past pulse waveform) exceeds a predetermined threshold. The predetermined threshold may be set by a user (e.g., by experiment) and may allow some variability from pulse waveform to pulse waveform without resulting in a flag event, but may be sufficient to identify an end-of-lamp-life condition prior to flashlamp failure.

Accordingly, the disclosed flashlamp degradation monitoring system and method may facilitate safer operation of a flashlamp by detecting when a flashlamp has reached an end-of-lamp-life condition without the need for taking the flashlamp out of service for visual inspection.

Although various embodiments of the disclosed flashlamp degradation monitoring system and method have been shown and described, modifications may occur to those skilled in the art upon reading the specification. The present application includes such modifications and is limited only by the scope of the claims.

What is claimed is:

1. A method for monitoring degradation of a flashlamp comprising:
   triggering the flashlamp to create a plasma and produce a light pulse corresponding to the created plasma;
   obtaining a plurality of values of a first parameter as a function of time during the produced light pulse to generate a pulse waveform of the produced light pulse;
   retrieving a reference pulse waveform of a reference light pulse, the reference pulse waveform including a plurality of values of the first parameter as a function of time during the reference light pulse;
   comparing the generated pulse waveform of the produced light pulse to at least the reference pulse waveform to determine a difference therebetween; and
   flagging an end-of-lamp-life condition when the difference exceeds a predetermined threshold, wherein the flagging step comprises preventing firing of the flashlamp.

2. The method of claim 1 wherein the flashlamp comprises an ionizable gas sealed in an envelope.

3. The method of claim 2 wherein the ionizable gas comprises xenon.

4. The method of claim 2 wherein the triggering step comprises applying a voltage having a magnitude sufficient to initiate ionization of the ionizable gas.

5. The method of claim 1 wherein the obtaining step comprises electronically obtaining the first parameter.

6. The method of claim 5 wherein the first parameter is electric current.

7. The method of claim 5 wherein the first parameter is voltage.

8. The method of claim 1 wherein the obtaining step comprises optically obtaining the first parameter.

9. The method of claim 8 wherein the first parameter is light energy.

10. The method of claim 1 further comprising storing the pulse waveform.

11. The method of claim 1 wherein the reference pulse waveform comprises a pulse waveform from a previous light pulse.

12. The method of claim 1 wherein the comparing step comprises at least one of a cross-correlation analysis, a derivative analysis and a linear approximation analysis.

13. The method of claim 1 wherein the predetermined threshold is of a magnitude sufficient to allow normal pulse waveform-to-pulse waveform variation without flagging the end-of-lamp-life condition.

14. The method of claim 1 wherein the flagging step comprises providing at least one of a visual indication and an audible indication of the end-of-lamp-life condition.

15. The method of claim 1 further comprising:
   charging one or more capacitors;
   discharging the one or more capacitors to pass a current when the trigger initiates ionization of a gas within the flashlamp, thereby producing a high-current pulse sufficient to create the plasma and produce the light pulse corresponding to the created plasma.

16. The method of claim 1 wherein the produced light pulse has a duration ranging from about 0.001 seconds to about 0.005 seconds.

17. The method of claim 1 wherein the first parameter is an electric current, a voltage, or a magnitude of light.

18. A flashlamp degradation monitoring system comprising:
- a flashlamp comprising an envelope housing an ionizable gas and opposed electrodes;
- a power supply electrically coupled to the electrodes;
- a trigger positioned to initiate ionization of the ionizable gas to create a plasma and produce a light pulse corresponding to the created plasma;
- a sensor positioned to obtain a plurality of values of a first parameter as a function of time during the produced light pulse to generate a pulse waveform of the produced light pulse; and
- a computer in communication with the sensor, wherein the computer is configured to retrieve a reference pulse waveform of a reference light pulse, the reference pulse waveform including a plurality of values of the first parameter as a function of time during the reference light pulse, to compare the generated pulse waveform with at least the reference pulse waveform to determine a difference therebetween, and to flag an end-of-lamp-life condition when the difference exceeds a predetermined threshold.

19. The system of claim 18 wherein the sensor is current sensor or a voltage sensor.

20. The system of claim 18 wherein the sensor is an optical detector.

21. The system of claim 20 further comprising a lens positioned to focus the light pulse onto the optical detector.

22. The method of claim 18 wherein the first parameter is an electric current, a voltage, or a magnitude of light.

* * * * *